United States Patent [19]

Feinstein

[11] Patent Number: 4,718,433

[45] Date of Patent: * Jan. 12, 1988

[54] CONTRAST AGENTS FOR ULTRASONIC IMAGING

[76] Inventor: Steven B. Feinstein, 295 Hasting Ave., Highland Park, Ill. 60035

[*] Notice: The portion of the term of this patent subsequent to Feb. 25, 2003 has been disclaimed.

[21] Appl. No.: 805,975

[22] Filed: Dec. 5, 1985

Related U.S. Application Data

[63] Continuation-in-part of Ser. No. 461,664, Jan. 27, 1983, Pat. No. 4,572,203.

[51] Int. Cl.⁴ .............................................. A61B 10/00
[52] U.S. Cl. .................................... 128/660; 128/661; 530/427
[58] Field of Search ............................. 128/660–663; 424/2, 9; 530/427; 523/300

[56] References Cited

U.S. PATENT DOCUMENTS

| | | | |
|---|---|---|---|
| 4,276,885 | 7/1981 | Tickner et al. ...................... | 128/660 |
| 4,466,442 | 8/1984 | Hillmann et al. . | |
| 4,500,358 | 2/1985 | Mayer et al. ........................ | 206/5 X |
| 4,548,736 | 10/1985 | Müller et al. .................... | 530/427 X |
| 4,572,203 | 2/1986 | Feinstein ............................. | 128/661 |

OTHER PUBLICATIONS

Tickner, E. G. et al "Noninvasive Assessment of Pulmonary Hypertension Using the Buffle Ultrasonic Resonance Pressure (BURP) Method" National Technical Information SVC Dept #HR-62917-1A, Apr. 1977.
Feinstein et al. (1984), JACC 3:14–20.
Cate et al. (1984), JACC 3:21–27.
Ophir et al., "US Backscatter from Constant Producing Collagen Microspheres, US Imag 2 (1980), pp. 67–77.
Bommer et al., Abs., 53rd Scientific Sess., Nov. 17–20 (1980), American Heart Association Meeting.
Bommer et al., Abs., CIRC, Amer. J. Cardiology, vol. 47, 403 (1981).

Primary Examiner—Francis J. Jaworski
Attorney, Agent, or Firm—Tilton, Fallon, Lungmus & Chestnut

[57] ABSTRACT

A method of ultrasonic imaging for use in medical procedures is disclosed. The method comprises providing specifically defined microbubbles formed by sonicating a bicompatible liquid comprising a sonicated aqueous protein solution, preferably a 5% solution of human serum albumin, and denaturing the protein therein by heat or chemical methods; injecting the microbubbles into an animal or human to thereby alter the acoustic properties of an area to be imaged; and then ultrasonically scanning the area so as to obtain an ultrasound scanning image.

9 Claims, 2 Drawing Figures

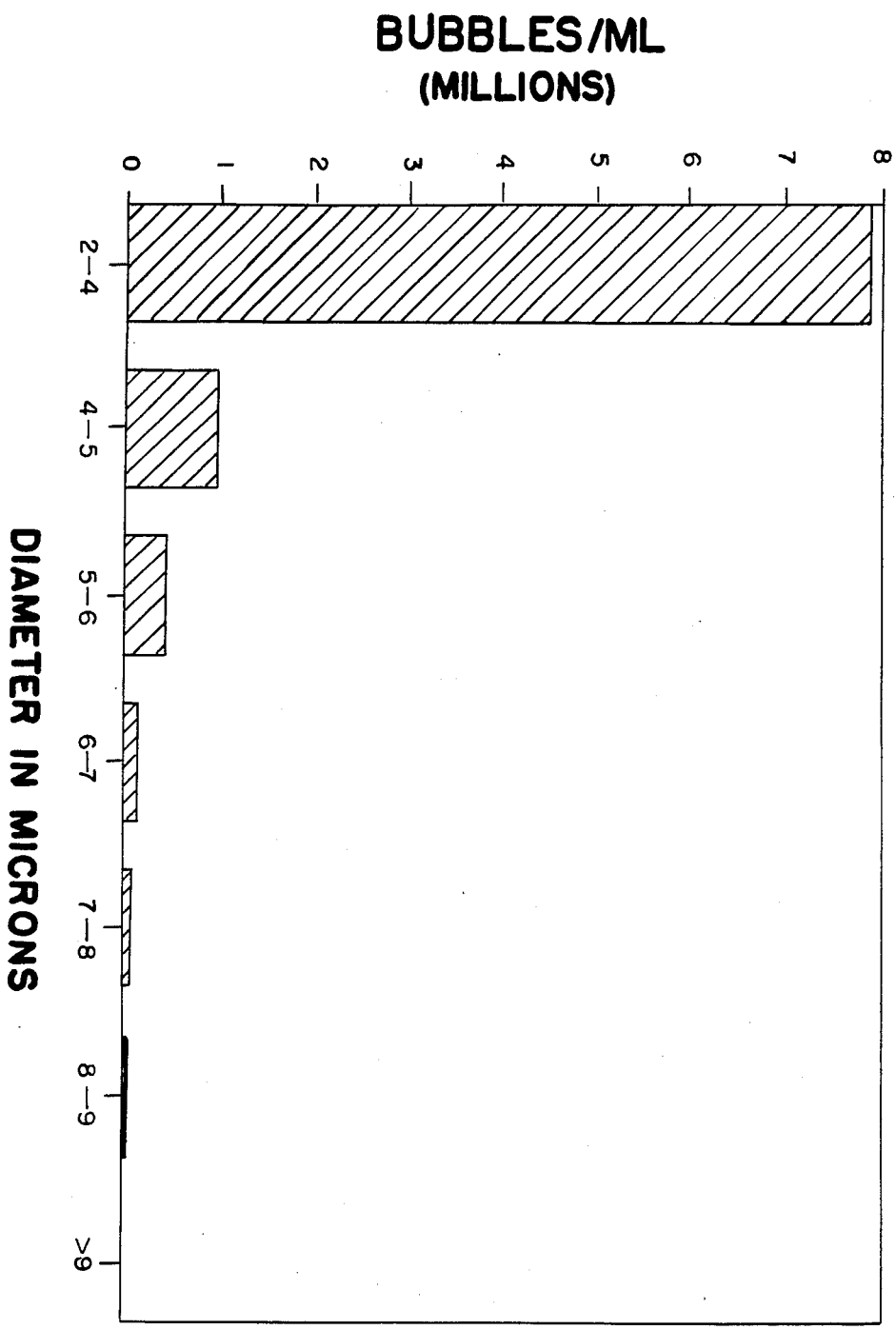

CONTRAST AGENTS FOR ULTRASONIC IMAGING

This is a continuation-in-part application of U.S. patent application Ser. No. 461,664 filed on Jan. 27, 1983 now U.S. Pat. No. 4,572,203.

BACKGROUND OF THE INVENTION

1. Field of the Invention

This invention relates to the field of ultrasonic imaging techniques, and more specifically, to a medical procedure which utilizes these techniques as a diagnostic tool.

2. DESCRIPTION OF THE PRIOR ART

Various technologies exist in which parts of an animal or human body may be imaged so as to aid in diagnosis and therapy. Some of these existing techniques are described in this section.

One of the most well known imaging techniques involves the use of X-rays to visualize skeletal and other internal structures within animals and humans. There are, however, a number of problems associated with the use of X-rays. First, some areas of the body may not be X-rayed safely. In addition, X-rays are dangerous if the amount of exposure is excessive; further, all X-ray radiation absorbed over a lifetime is cumulative. Finally, while X-rays may produce images of the skeletal and other internal structures, X-rays have proved to be relatively unsatisfactory for detailed viewing of certain organ systems and blood vessels.

Another widely used technique is angiography, whereby a radio-opaque dye is injected into an artery. Because the dye highlights the arteries through which it flows, an X-ray may be used to obtain an image of major, large arteries and their significant branches. However, angiography does not permit visualization of under-perfused, ischemic areas of tissue or heart muscle, or the microcirculation. In addition, certain angiographic observations are based upon measurements which may vary depending upon the apparatus used, the placement and angle of lenses, operator skill and similar factors. Moreover, angiography is invasive in that it requires the placement of a catheter into arteries as opposed to veins. Besides requiring hospitalization, angiography may be dangerous.

Another technique, often referred to as radio-nuclide imaging, involves the injection of radioactive substances, such as thallium, into the blood stream. This technique does not require invasion of the arteries as does angiography, but it does require the use of very expensive and sophisticated machinery. Further, radio-nuclide imaging produces images of only a limited number of views of the heart, and those images may not be of exceptional clarity. Finally, this type of radiation is cumulative over a lifetime and may be dangerous.

Recently, there have been advances in techniques for ultrasonically imaging various parts of the body; these techniques when applied to the heart in particular are known as "echocardiography." An ultrasonic scanner is used to generate and receive sound waves. The ultrasonic scanner is placed on the body surface overlying the area to be imaged. The sound waves generated by the scanner are directed toward the area to be imaged. The scanner then detects sound wave reflected from the underlying area and translates that data into images.

While such ultrasonic scanners are known in the art, a brief review will be set forth in order to more fully explain the present invention. When ultrasonic energy is transmitted through a substance, the acoustic properties of the substance will depend upon the velocity of the transmissions and the density of the substance. Changes in the substance's acoustic properties (or acoustic impedance) will be most prominent at the interface of different substances (i.e., solids, liquids and gases). As a consequence, when ultrasonic energy is directed through various media, the changes in acoustic properties will change the reflection characteristics, resulting in a more intense sound reflection signal received by the ultrasonic scanner.

Early ultrasonic imaging techniques such as echocardiograms suffered from a lack of clarity. As a result, extensive efforts were undertaken to improve the ultrasonic scanners and related equipment. In addition, beginning in 1968, "contrast" agents were injected into the blood stream in an effort to obtain clearer or "enhanced" ultrasonic images. The prior art contrast agents were liquids containing microbubbles of gas, which sometimes were claimed to be encapsulated with gelatin (see U.S. Pat. No. 4,276,885 or saccharine and sometimes were produced by mechanically agitating, i.e. handshaking, mixtures of various liquids. Other prior art contrast agents are disclosed in an article by J. Ophir, et al. entitled "Ultrasonic Backscatter from Contract Produced by Collagen Microspheres" in Ultrasonic Imaging 2 (1980) pp. 66–77.

The contrast agents themselves are intense sound wave reflectors because of the acoustic differences between the liquid and the gas microbubbles dissolved therein; thus, when the contrast agents are injected into and perfuse the microvasculature of tissue, clearer images of such tissue may be produced. However, notwithstanding the use of such contrast agents, the image produced, for example of the myocardial tissue, is of relatively poor quality, is highly variable and is not quantifiable due to the variable size and persistence associated with prior art microbubbles. Further, the problems of air embolism toxicity have not yet been investigated.

SUMMARY OF THE INVENTION

The present invention is directed to an improvement associated with such prior art contrast agents by which smaller and more uniform microbubbles are produced. A second embodiment is directed to the novel use of specifically defined semi-solid contrast agents.

The contrast agents of the present invention are (1) echogenic (i.e., capable of reflecting sound waves); (2) small enough to pass through capillaries so as to perfuse tissue previously inaccessible to the prior art contrast agents injected into a peripheral venous site, thereby producing enhanced images of such tissue and organs and permitting differentiation between well-perfused and poorly-perfused tissue; (3) quantifiably reproducible; and (4) sufficiently stable to be stored for reasonable periods of time prior to use.

The method of the present invention (1) permits the imaging of organ systems which could not be imaged using prior art ultrasonic techniques, and (2) permits clearer, more detailed imaging of certain areas which were viewable using such prior art techniques.

In the preferred embodiment of the present invention, a viscous protein solution (e.g., 5% human serum albumin) is subjected to high frequency (5,000 to 30,000 Hz) ultrasonic energy. As a result, microbubbles having a diameter of approximately 6 to 20 microns are produced. The 5% albumin solution shows the best results in forming small microbubbles, primarily having a diameter in the range of 2-4 microns. For ease of reference such microbubbles will be referred to herein as "sonicated" microbubbles. As described in great detail hereinbelow, such sonicated microbubbles have been found to be improved contrast agents.

The microbubbles or microspheres comprising protein or derivatives thereof in an aqueous solution are formed into stable contrast agents by any of a number of methods known in the art for physically (via heat) or chemically altering the protein or derivatives to denature or fix the material. For example, the use of heat applied to the contrast agent after formation thereof, or during formation as a result of the sonication of the same is one method for denaturing the protein material to form stable contrast agents. As a second method, fixation (i.e. chemical denaturation) of the protein material using formaldehyde or gluteraldehyde may also be utilized to form stable contrast agents.

The contrast agents of the present invention are detected by conventional ultrasonic scanning equipment and translated into images in the manner described above. The use of the microparticles is especially advantageous in that it obviates the need to introduce gaseous bubbles as contrast agents in the human or animal system, and thus eliminates the air embolism toxicity risks inherent in that procedure. Depending upon whether the microparticles are to be used exclusively in animal research or for diagnostic and therapeutic purposes, the potential biocompatability of the particular type of microparticle is a significant consideration.

Thus, while overcoming many of the problems associated with the prior art, the present invention makes possible the production of unique images of various organ systems. Although the invention technique is applicable to various animal and human body organ systems, its novel features and advantages may be better understood from the following description of its use in obtaining images of myocardial tissue and perfusion or blood flow patterns.

BRIEF DESCRIPTION OF THE DRAWINGS

The invention will now be described with reference to the accompanying drawings, wherein:

FIG. 2 is a graph of the size distribution of microspheres of a sonicated 5% human serum albumin solution.

DETAILED DESCRIPTION OF THE INVENTION

Figure 1:
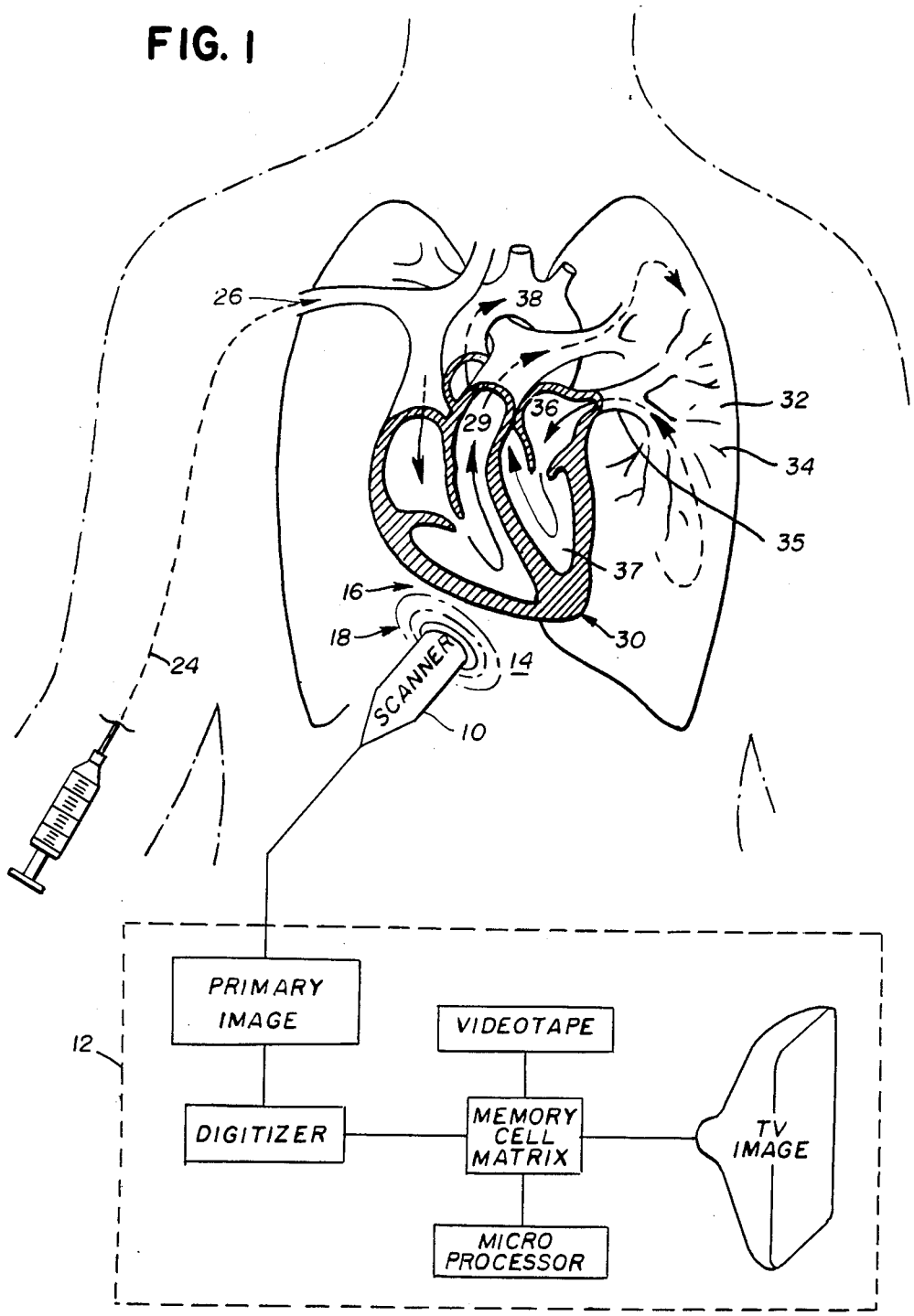
FIG. 1 is a schematic view showing the use of an ultrasonic scanner in echocardiography.

FIG. 1 is a schematic view of the heart and lungs, as well as of ultrasonic scanning equipment consisting of a scanner 10 and imaging apparatus 12. The equipment produces visual images of a predetermined area, in this case, the heart region of a human body. Typically, the scanner 10 is placed directly on the skin 14 over the area to be imaged 16. The scanner 10 houses various electronic components including ultrasonic transducers. The scanner 10 produces ultrasonic waves 18 which perform a sector scan of the heart region 16. The ultrasonic waves 18 are reflected by the various portions of the heart region 16 and are received by the generating transducer and processed in accordance with pulse-echo methods known in the art. After processing, signals are sent to the imaging apparatus 12 (also well known in the art) for viewing.

In the method of the present invention, after the patient is "prepped" and the scanner 10 is in place, the sonicated microbubble or microparticle contrast agent is injected, for example, through an arm vein, generally indicated at 24. The contrast agent flows through the vein 24 in the direction of the arrow 26, through the right venous side 28 of the heart 30, through the main pulmonary artery 29 leading to the lungs 32, across the lungs 32, through the capillaries 34, into the pulmonary vein 35 and finally into the left atrium 36 and the left ventricular cavity 37 of the heart 30.

The present invention is directed to both sonicated microbubbles and microparticulate matter used as contrast agents. It has been found that the use of sonicated microbubbles produces images having vividly contrasting areas. In particular, such microbubbles (1) may be biocompatible or biodegradable, (2) are small enough to pass through the capillary beds which are about 8 to 10 microns in size and (3) have acoustic properties making them echogenic. While not to be bound by any theory, the sonicated microbubbles of the present invention produce noticeably clearer and more detailed images of the myocardial tissue and microvasculature, as compared with prior art contrast agents.

The following is a procedure described in my U.S. Pat. No. 4,572,203, microbubbles were produced from a mixture of Renografin-76 (a relatively non-toxic, biocompatable radio-opague dye well known in the art) and saline in a one-to-one ratio. This mixture was sonicated, i.e. subjected to high frequency energy, for about 30 seconds by a Heat System 375 watt sonicator. Such sonicators are well known in the art for other uses, and usually emit ultrasonic energy of 20,000 Hz, although energies of 5,000 to 30,000 Hz or even higher are within the scope of the present invention.

In another presently preferred embodiment of the invention, a solution of protein or derivatives thereof, capable of forming microbubbles or microspheres when sonicated in accordance with the above-described proceduce, is used. One example of a useful solution is a 5% acqueous solution of human serum albumin, referred to herein as albumin. Albumin in solution is commercially available from any of a number of sources. While not being bound by any particular theory of operation, it appears that sonication of the solution under conditions discussed above causes the formation of microbubbles. The resulting microbubbles are substantially different from those prepared from solutions of dextrose, sorbitol, and Renografin in that the walls of the microbubbles are significantly more stable, thereby making the microbubbles themselves more stable. The stability of these microbubbles is believed to be a result of the fact that the sonicator heats the albumin to a temperature sufficient to denature the protein. As shown in FIG. 2, the sonication also creates bubbles primarily in the range of 2-4 microns. FIG. 2 illustrates the size distribution of microbubbles formed, as described above, out of a commercially available aqueous solution of 5% albumin. Substantially all of the microbubbles are in the range of 2-4 microns, as determined by a Coulter Counter, using techniques well-known in the art. Of the microbubbles produced, approximately 8 million per milliliter (ml.) of solution are in the 2-4 micron range, approximately 1 million microbubbles per ml. in the 4-5 micron range, less than 0.5 million microbubbles per ml. in the 5-6 micron range, and relatively negligible amounts of microbubbles in the range above 6 microns are formed. As shown in FIG. 2, substantially all of the microbubbles had diameters of less than 9 microns, and the predominant diameters were in the range from 2 to 5 microns.

As an alternative to heat treatment of the microbubbles as a result of sonication, the protein can be denatured and the microbubbles stabilized by heat treatment to a temperature in the range of 50° to 60° Centigrade, with the actual temperature in the range depending on the protein, proteins used or protein derivatives used. The specific temperature and conditions for denaturation of the various proteins which may be used for the present invention are generally known in the art.

The microbubbles formed from 5% albumin may, in the alternative, be stabilized to form a commercially, clinically usable contrast agent by treatment with various chemical agents which chemically denature, or "fix", the protein, and derivatives thereof. Chemical denaturation of the protein (or derivatives ) may be accomplished by either binding the protein with a difunctional aldehyde, such as gluteraldehyde. For the latter procedure of stabilizing the invented microbubble contrast agent, the microbubbles may be reacted with 0.25 grams of 50% acqueous gluteraldehyde per gram of protein at pH 4.5 for 6 hours. The treated contrast agent is then gently and extensively washed to remove as much of the unreacted gluteraldehyde as possible.

The microspheres formed from 5% albumin which has been sonicated as described are stabilized and exist for 48 hours or longer. This may be compared with the above-described sonicated sugar solutions which last a few minutes to a few hours. Thereafter, they are no longer effective contrast agents.

This invented echo contrast agent permits left heart imaging from intravenous injections. The sonicated albumin microbubbles, when injected into a peripheral vein is capable of transpulmonary passage. This results in echocardiographic opacification of the left ventricle (LV) cavity as well as myocardial tissue. The sonicated albumin microbubbles are small, stable and echo reflective targets.

A total of 72 intravenous injections of sonicated albumin microbubbles were performed in 5 dogs. Three to 10 ml of contrast solution, containing a minimum of 500,000 bubbles per ml, were injected into the dorsal forepaw vein in each trial. No significant changes were noted in heart rate, blood pressure or arterial blood gases. LV cavity opacification was graded from 0 (no opacification) to +3 (full LV opacification) with the duration noted in seconds. The overall successful transpulmonary opacification rate was 78% (56/72 trials). LV tissue opacification was always preceded by +3 LV capacity opacification. Successful transpulmonary passage of the sonicated albumin microspheres was observed if (a) the RV contrast opacification was +3 (b) the average sphere size was 4 microns, or less, and (c) the sphere concentration was at least one million per milliliter. The results are set forth below in Table 1.

TABLE 1

| LV Cavity Opacification | | |
|---|---|---|
| Grade | Trials | Contrast in LV cavity (seconds) |
| +3 | 11 | 20 ± 8 |
| +2 | 14 | 18 ± 8 |
| +1 | 31 | 12 ± 17 |

TABLE 1-continued

| LV Cavity Opacification | | |
|---|---|---|
| Grade | Trials | Contrast in LV cavity (seconds) |
| 0 | 16 | 0 |

Thus, as shown here, successful opacification of the LV cavity and myocardial tissue is now feasible using peripheral venous injections of sonicated albumin microspheres.

Besides the scanner 10 briefly described above, there exist other ultrasonic scanners, examples of which are disclosed in U.S. Pat. Nos. 4,143,554 and 4,315,435, the disclosures of which are herein incorporated by reference. Basically, these patents relate to various techniques including dynamic cross-sectional echography (DCE) for producing sequential two-dimensional images of cross-sectional slices of the animal or human anatomy by means of ultrasound energy at a frame rate sufficient to enable dynamic visualization of moving organs. Types of apparatus utilized in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable devices in a manner somewhat analogous to radar or sonar displays. While DCE can be used to produce images of many organ systems including the liver, gall bladder, pancreas and kidney, it is frequently used for visualization of tissue and major blood vessels of the heart.

Existing DCE scanners can be classified according to the geometry of their field of view (linear or sector scanning), according to the means used for scanning that field of view (mechanical or electronic scanning) and according to whether the transducer scans the patient or object through an intervening water bath or by direct contact with the surface of the object as, for example, the skin of a patient using an appropriate contact gel or oil. Linear scanners produce a scan of the anatomy consisting of a set of nominally parallel scan lines, displaced with respect to one another by a line spacing roughly comparable to the effective width of each line, as determined primarily by the transducers used in the apparatus. The cross-section imaged by such scanners is therefore approximately rectangular in shape, its width being determined by the line spacing and total number of lines, while its depth is determined by the penetration range of the ultrasound energy into the tissue. Linear scanners are generally used where there is a relatively extended region of the body surface from which access to the parts of interest of the anatomy is possible, such as in the abdominal organs.

Sector scanners produce a scan of the anatomy consisting of a fan of divergent lines spaced angularly from one another, but interesecting (nominally) at a point. The angular spacing is even or uneven, depending upon the apparatus, and is roughly comparable to the effective angular width of each line. Sector scanners are generally used where the anatomical window or region of the body surface from which access to the anatomical part of interest is relatively small, as in the adult heart, the brain and the eye.

Another type of sector scanner is mechanical in nature and can be further divided into two sub-classes, oscillating transducer scanners and rotating transducer scanners. An oscillating transducer scanner is one in which a single transducer is oscillated about an axis nominally line in the front plane and passing thorugh the center of the transducer with an appropriate angle sensor being used to monitor the angular position of the transducer at any time. In a typical rotating transducer scanner, several transducers pin inside a small dome filled with liquid, with one transducer at a time scanning the area of interest. These and other scanners are within the scope of the present invention.

As stated above, in attempting to find a safe, reproducible, quantifiable contrast agent for use in reproducing an enhanced ultrasonic image of the tissue under study, researchers have used saccharin and gelatin encapsulated microbubbles of nitrogen or carbon dioxide gas having a mean size of approximately 75 microns, pressurized gas in liquids (e.g., $H_2O_2$), and mechanically agitated (hand shaken) mixtures of liquid solutions. However, since the pulmonary artery capillaries are about 8 to 10 microns in diameter, the 75 micron encapsulated microbubbles may not cross the capillary bed and, as a result, their use would require a direct injection into the area to be imaged or an arterial injection involving the same risks as the invasive approach of angiography discussed above. Further, microbubbles produced by agitating various liquids other than by sonicating them have wide variability of size. Variable amounts of such non-encapsulated agitated microbubbles can pass thorugh capillaries, but the present state of the art has only produced qualitative data due to the inability to control the variables described above. These contrast agents all work to some degree, but suffer from a number of problems including the fact that the size of the bubbles is not uniform. These and other problems are overcome by the sonicated microbubbles of the present invention.

However, while sonicated microbubbles are more uniform in size and produce enhanced images, the potential problems associated with the introduction of air remain. The danger of injecting micro-bubbles, encapsulated or not, into the heart is that the bubbles eventually collapse and the amount of dissolved air may be toxic in the arterial system (e.g., of the brain and kidneys) as well as in other microcirculatory systems.

Thus, it is evident that the particular contrast agent selected will depend upon the purpose of the imaging. For example, an agent's potential risk factors should be considered for diagnostic or therapeutic uses. The size of the contrast material is also of concern. If the particles are too large they will not pass through the capillaries and thus will require direct or arterial injections if the area to be imaged lies beyond the capillaries. On the other hand, if the contrast agent is too small, it may not reflect sound waves emitted by the ultrasonic transducer.

The microparticles may be used for imaging a wide variety of areas, even when injected at a peripheral venous site. Those areas include (without limitation): (1) the venous drainage system to the heart; (2) the myocardial tissue and perfusion characteristics during an exercise treadmill test or the like, and (3) myocardial tissue after an oral ingestion or intravenous injection of drugs designed to increase blood flow to the tissue. Additionally, the microparticles may be useful in delineating changes in the myocardial tissue perfusion due to interventions such as: (1) coronary artery vein grafting; (2) coronary artery angioplasty (balloon dilatation of a narrowed artery); (3) use of thrombolytic agents (such as streptokinase) to dissolve clots in coronary arteries; or (4) perfusion defects or changes due to a recent heart attack.

Furthermore, at the time of a coronary angiogram (or a digital subtraction angiogram) an injection of the microparticles may provide data with respect to tissue perfusion characteristics that would augment and complement the data obtained from the angiogram procedure, which identifies only the anatomy of the blood vessels.

Through the use of the microbubbles of the present invention, other non-cardiac organ systems including without limitation the liver, spleen, kidney, etc. that are presently imaged by ultrasonic techniques may be susceptible to an enhancement of such currently obtainable images, and/or the generation of new images showing perfusion and flow characteristics that had not previously been susceptible to imaging using prior art ultrasonic imaging techniques.

Having described the invention, it is obvious that other modifications may be made by those skilled in the art. For example, other water soluble polymers can be used in place of albumin including hemoglobin, and other magnetic particles can be used in place of magnetite, etc., including magnetic iron oxides, carbonyl iron and the like. This invention, therefore, is to be limited only to the scope and spirit of the appended claims.

What is claimed is:

1. The method of ultrasonic imaging in which microbubbles are injected into a mammal to alter the accoustic properties of a predetermined area which is then ultrasonically scanned to obtain an image of the area for use in medical procedures, wherein the improvement comprises the steps of forming an aqueous protein solution, subjecting said solution to high frequency sonication while heating the solution sufficiently to denature portions of the protein, said sonication forming microbubbles of relatively uniform size stabilized by the denatured protein, and using the stabilized microbubbles as an injectate for said ultrasonic imaging.

2. The method of claim 1 in which the improvement further comprises forming said aqueous protein solution from albumin.

3. The method of claim 1 in which the improvement further comprises forming said stabilized microbubbles with substantially all of the microbubbles having diameters less than 9 microns.

4. The method of claim 1 in which the improvement further comprises forming said stabilized microbubbles with the microbubbles having diameters predominantly in the range from 2 to 5 microns.

5. The method of claims 1, 3, or 4 in which said stabilized microbubbles are used by injection into a peripheral vein for ultrasonic heart imaging via transpulmonary passage.

6. The method of ultrasonic imaging in which microbubbles are injected into a mammal to alter the accoustic properties of a predetermined area which is then ultrasonically scanned to obtain an image of the area for use in medical procedures, wherein the improvement comprises the steps of forming an aqueous protein solution, subjecting said solution to high frequency sonication while heating the solution sufficiently by means of the sonication to denature portions of the protein, said sonication forming microbubbles stabilized by the denatured protein with substantially all of the microbubbles having diameters less than 9 microns, and using the stabilized microbubbles as an injectate for said ultrasonic imaging.

7. The method of claim 6 in which the improvement further comprises forming said protein solution from human serum albumin.

8. The method of claims 6 or 7 in which the improvement further comprises forming said stabilized microbubbles with the microbubbles having diameters predominantly in the range from 2 to 5 microns.

9. The method of claims 6 or 7 in which said stabilized microbubbles are used by injection into a peripheral vein for ultrasonic heart imaging via transpulmonary passage.

* * * * *